US00PP37526P2

(12) United States Plant Patent
Hansen

(10) Patent No.: US PP37,526 P2
(45) Date of Patent: Jul. 21, 2026

(54) ***HOSTA* PLANT NAMED 'Gold Medal'**

(50) Latin Name: ***Hosta* hybrid (Tratt.)**
Varietal Denomination: Gold Medal

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,961

(22) Filed: Dec. 11, 2025

(51) Int. Cl.
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/12
See application file for complete search history.

*Primary Examiner* — Kent L Bell

(57) ABSTRACT

A new and distinct *Hosta* plant named 'Gold Medal' producing small-sized, low, rounded mounds of basal, nearly rounded leaves with mucronulate apices. The bases are cordate with lobes divergent and not meeting. The leaves begin chartreuse in the spring and become a bright yellow with sufficient sunlight as the season progresses. The campanulate flowers have tepals with near-white edges and light lavender center stripes, and are held just above the foliage beginning in early July. 'Gold Medal' is useful in the landscape, as a container plant, a specimen or en masse.

2 Drawing Sheets

Botanical classification: *Hosta* hybrid (Tratt.).
Variety denomination: 'Gold Medal'.

STATEMENT REGARDING PRIOR DISCLOSURES UNDER 37 CFR 1.77(B)(6)

*Hosta* 'Gold Medal' was first introduced by the inventor as a non-enabling description in registration of the name in early 2025 with the International Cultivar Registration Authority for the genus *Hosta*. No plants of *Hosta* 'Gold Medal' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Gold Medal' hereinafter also referred to as the new plant or by the cultivar name 'Gold Medal'. *Hosta* 'Gold Medal' was hybridized by the inventor on Jul. 5, 2021, at a wholesale perennial nursery in Zeeland, Michigan, USA. The female parent was 'Age of Gold' U.S. Plant Pat. No. 30,902 and the male parent was the proprietary, unnamed unreleased proprietary seedling of 'Blue Mouse Ears' (not patented). The seeds from this cross were planted in the spring of 2022 and a single seedling selection from this cross eventually produced the new plant. The new plant was assigned the breeder code 21-738-4 and passed the initial evaluation in the summer of 2022.

'Gold Medal' has been asexually propagated by division at the same nursery since 2023 and also by careful shoot tip plant tissue culture with the resultant asexually propagated plants having retained all the same traits as the original plant. *Hosta* 'Gold Medal' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have yellowish leaf blades. The most similar *Hosta* cultivars known to the applicant are: 'Blue Mouse Ears' (not patented), 'Gold Drop' (not patented), 'Golden Goal' (not patented), 'Golden Jubilee' (not patented), 'Golden Prayers' (not patented), 'Golden Scepter' (not patented), 'Golden Torch' (not patented), and 'Sun Mouse' U.S. Plant Pat. No. 30,033.

'Age of Gold' is larger and more mounded and less upright in habit with larger, yellow foliage, and a faster growth rate. The male parent has green foliage and a smaller, thicker, and, rounder leaf blade.

'Blue Mouse Ears' has a slightly smaller habit, similar but smaller leaf shape, faster growth rate, and the leaves are medium green with slight glaucous surfaces. 'Gold Drop' has a more ovate and less rounded leaf with more chartreuse color, and the growth rate is faster. 'Golden Goal' has a more glaucous and chartreuse foliage, the apex is more broadly acute, and the base is more cordate with nearly overlapping lobes. 'Golden Jubilee' has more lustrous ovate foliage. 'Golden Prayers' has smaller foliage that is more ovate with more acute apices and more cordate nearly overlapping lobes, and the surface is more bullate. 'Golden Scepter' has smaller foliage with lighter substance that is more ovate, the flowers are deeper purple, and the growth rate is faster. 'Golden Torch' has a larger habit, and more ovate and less rounded foliage. 'Sun Mouse' is a smaller plant with smaller foliage and flowers of light purple. The new plant has leaf blades as thick as 'Blue Mouse Ears' and thicker than all the other above comparison plants.

Other *Hosta* cultivars may have individual traits similar to 'Gold Medal' but the new plant differs from the above listed cultivars and all other *Hostas* known to the applicant, by the combination of the following traits.

1. Leaves are small-sized, nearly rounded, very thick substance, with mucronulate apices and cordate bases with divergent lobes that do not overlap;
2. Leaves are flat, not bullate between the veins, and slightly impressed adaxial veins with a mucronulate apex;
3. Leaf color emerges chartreuse becoming more yellow as the season progresses;
4. Campanulate flowers are near white along tepal edges with pale lavender centers on erect chartreuse-colored scapes beginning in early-July;
5. Flowers are densely arranged on scapes with the first flowers beginning to open just above the foliage;
6. The habit is a small-sized, low, rounded mound.

BRIEF DESCRIPTION OF THE DRAWING

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

The drawings show a potted three-year-old plant of 'Gold Medal' in a partially shaded greenhouse at a nursery in Zeeland, MI with supplement fertilizer and water as needed.

DETAILED BOTANICAL DESCRIPTION

Figure 1:
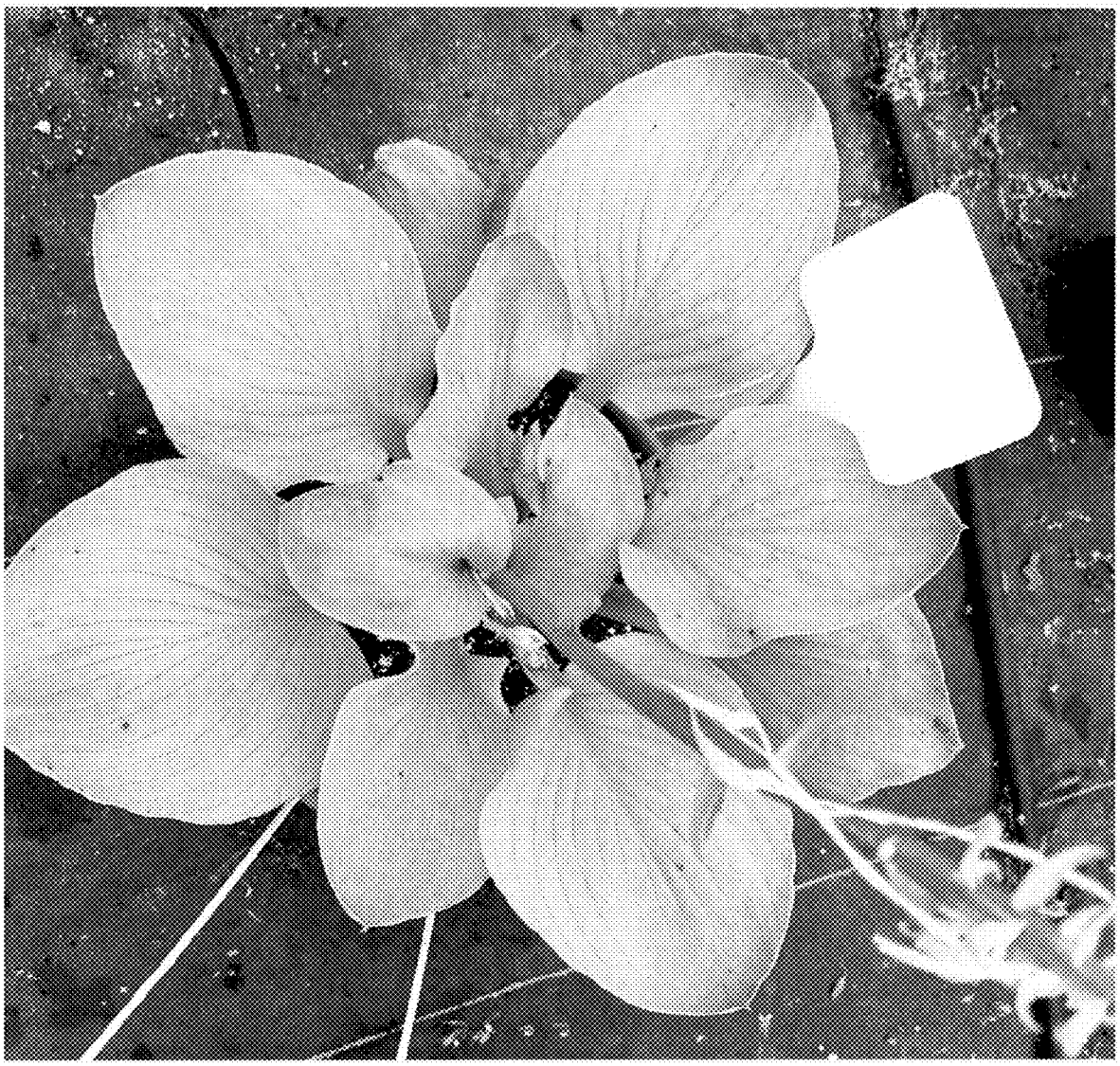
FIG. 1 shows the landscape foliage habit of a plant in late summer.
Figure 2:
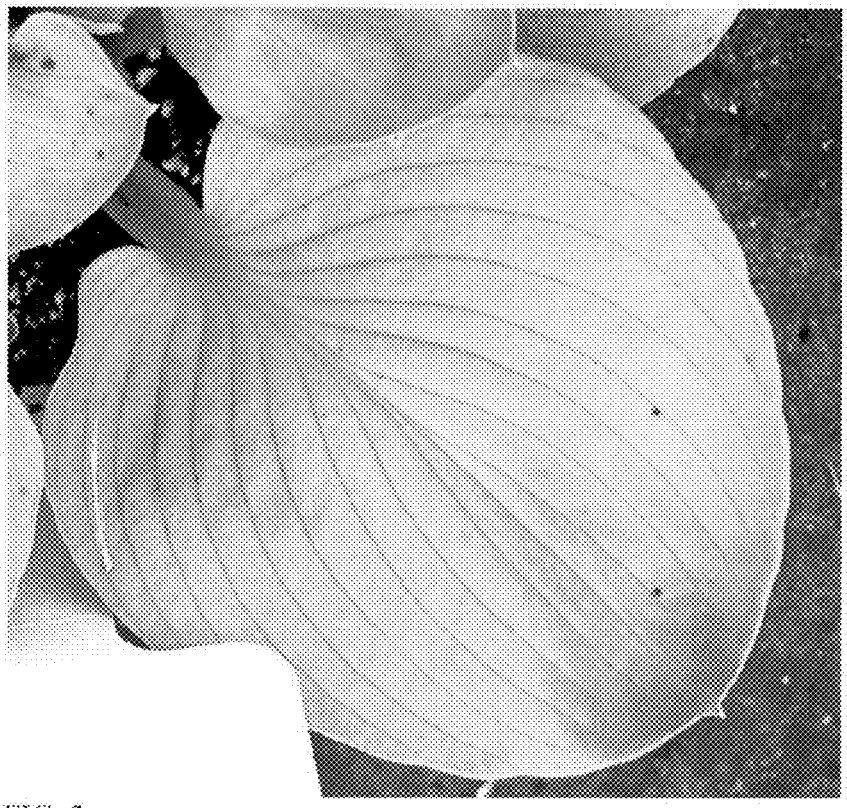
FIG. 2 shows a close-up of a leaf of a plant.
Figure 3:
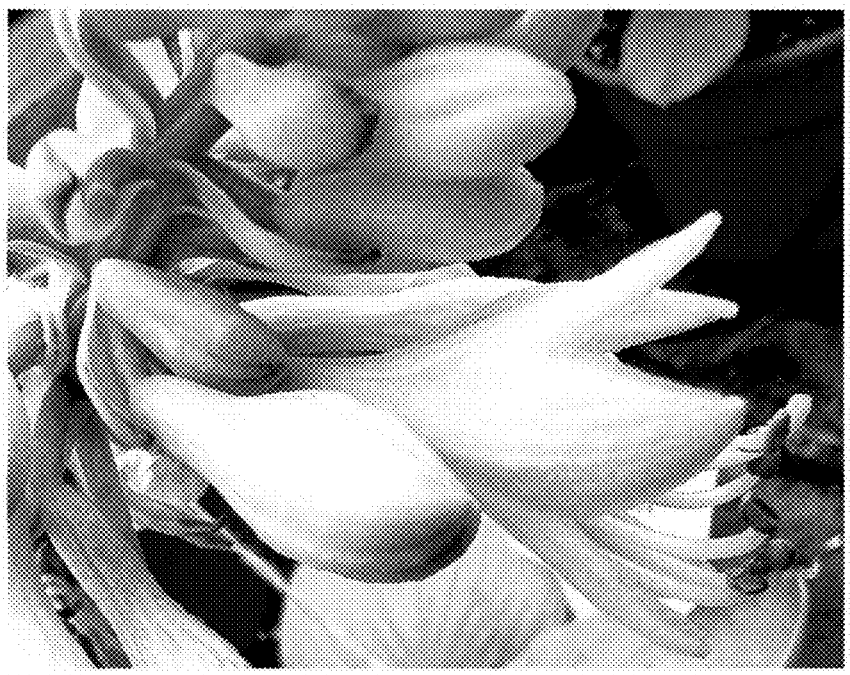
FIG. 3 shows a close-up of the buds and flower.

The following descriptions and color references are based on the 2015 edition of The Royal Horticultural Society Colour Chart except where common dictionary terms are used. The new plant, *Hosta* 'Gold Medal', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a six-year-old plant in a shaded trial garden in Zeeland, Michigan with supplemental water and fertilizer.

Botanical classification: *Hosta* x hybrid;

Parentage: Female or seed parent is 'Age of Gold'; male or pollen parent is an unnamed seedling of 'Blue Mouse Ears';

Propagation: Garden division and sterile shoot tip tissue culture;

Time to initiate roots from tissue culture: About three weeks;

Growth rate: Moderate;

Crop time: About three months to five months to finish during the spring in a one-liter container from rooted tissue culture plantlet during the warm portion of the growing season;

Rooting habit: Fleshy, lightly branching; to about 2 mm diameter;

Root color: Nearest RHS NN155C when actively growing;

Plant shape and habit: Hardy herbaceous perennial with basal rosette of leaves emerging from rhizomes producing a small-sized low mound of slightly upwardly to outwardly pointing petioles and leaves and mostly upwardly angled scapes flowering slightly above the foliage;

Plant size: Foliage height to about 21 cm above soil line to the top of the leaves, about 46 cm tall to the top of the flower scapes, and to about 36 cm wide at the widest point about 16 cm above the soil line;

Foliage description: Nearly rounded; rounded mucronulate apex, cordate base with lobes divergent and not meeting at petiole; margin entire; flat to slightly convex toward apex, not bullate; glabrous and matte both surfaces; flexible; not variegated; four to six per division;

Leaf blade size: To about 15 cm long and about 13 cm wide about the middle of the blade;

Leaf blade color: Early season and expanding adaxial nearest RHS 144B, abaxial between RHS 144C and RHS 144B; mid-season and mature adaxial variable, between RHS N144D and RHS 145A in portions protected from high light exposure, and nearest RHS 4B in portions exposed to high light, abaxial variable, nearest RHS 11B and between RHS 11B and RHS 145B;

Veins: 10 to 11 pairs with midrib; adaxial veins sunken or furrowed; costate and smooth abaxial;

Vein color: Adaxial nearest RHS 147C and abaxial nearest RHS 146D;

Petiole: Glabrous and matte both adaxial and abaxial; moderately concavo-convex proximally and shallowly distally; stiff; aspect outwardly and upwardly; to 13 cm long, 12 mm wide below blade, 14 mm wide at base and about 6 mm deep at base and 4 mm wide below leaf blade, average about 11 cm long, 11 mm wide and 4 mm deep near middle;

Petiole color: Adaxial between RHS 144A and RHS 144B; abaxial midrib nearest RHS 145C and region surrounding midrib between RHS 145C and RHS 147D;

Flower description:

Buds one to two days prior to opening: Clavate; rounded apex and narrow tube and rounded base; about 24 mm long and 10 mm in diameter at the widest portion in the bulb, tube to about 8 mm long and to about 5 mm diameter near base, gradually tapering from bulb;

Bud color: Distal one-half of bulb nearest RHS NN155C with faint blush of nearest RHS 85D, proximal one-half of bulb nearest RHS 85D with the apical 2 mm and tepal edges nearest RHS 85C, and corolla tube between RHS NN155D and RHS 85D;

Inflorescence: Flowering portion about 14 cm long and 10 cm wide; with bracts subtending each flower;

Flower bracts: Typically, one subtending each flower; ovate; navicular; stiff; acute apex; truncate and clasping base; entire margin; glabrous and slightly lustrous abaxial and adaxial;

Flower bract color: Adaxial and abaxial 1 mm wide edge transparent to blushed with nearest RHS 85C, next 1 to 2 mm inner margin variable with proximal bracts between RHS 144A and RHS 144B and distal bracts nearest RHS 6D, adaxial and abaxial longitudinal center between RHS NN155B and RHS NN155A;

Flowers: Perfect; incomplete; campanulate; aspect outwardly; to about 42 mm long to exserted pistil; corolla to 33 mm long and 23 mm wide at apex, fused in basal 20 mm, free in the distal 13 mm, decreasing in size distally; corolla tube portion 13 mm long, 8 mm wide at fusion, and gradually tapering to 5 mm diameter in middle; with rounded base; flowers tightly arranged on scape;

Flowering lasting: Persists for a normal period, usually about one day on plant;

Flowering period: Scapes remain effective with flowers beginning early July for about three weeks; with about 48 flowers per scape; mostly non-secund;

Fragrance: No detectable fragrance;

Tepal: Two sets of three; lanceolate; entire margins; acute apex; fused in basal 20 mm and free in the distal 13 mm; glabrous adaxial and abaxial; outer set to about 9 mm wide and 35 mm long; inner set to about 8 mm wide and 35 mm long; inner set with a 1 mm wide translucent to transparent margin;

Tepal color: Outer and inner sets identical; adaxial longitudinal center nearest RHS 85D and RHS NN155D along the margins and the corolla tube, abaxial nearest RHS NN155D with a faint blush of nearest RHS 85D in the blade and the corolla tube;

Gynoecium: Single; to about 44 mm long; superior;

*Style*.—Cylindrical; glabrous; to about 36 mm long and 1 mm diameter; straight with distal 4 mm arcuate upwards 90°; color nearest RHS 155B distally and proximally nearest RHS 145D.

*Stigma*.—Globose; puberulent; about 1 mm long and 1.5 mm diameter; color nearest RHS 155B.

*Ovary*.—Ellipsoidal; superior; apex acute; base rounded to truncate; sides deeply furrowed; about 7 mm long and 3 mm diameter; color between RHS 145A and RHS 144B.

Androecium: Six;

*Filaments*.—Six; cylindrical; approximately 40 mm long and 0.5 mm in diameter; arcuate upwardly about 90° in the distal 10 mm; color nearest RHS NN155B distally and proximally between RHS 155C and RHS 145D.

*Anthers*.—Oblong; with rounded ends; dorsifixed; longitudinal; about 4 mm long and 2.2 mm wide when fully developed in unopened flower; color adaxial with alternate longitudinal lines of nearest RHS 164B and RHS 15C, abaxial nearest RHS 16C.

*Pollen*.—Abundant; spherical; less than 0.1 mm long; color nearest RHS 17B.

Peduncle: Cylindrical; stiff; one per mature division; about 5 per plant; glabrous; glaucescent; aspect upwardly; to about 46 cm long, and about 10 mm in diameter at base, average about 43 cm long and 8.5 mm diameter at base;

Peduncle color: Proximally nearest RHS 146C, distally nearest RHS 144B;

Pedicel: Cylindrical; glabrous; slightly lustrous; to about 13 mm long and 3.5 mm diameter; slightly arcuate laterally; attitude outwardly;

Pedicel color: Proximally nearest RHS 145A, distally nearest RHS 4D;

Bracts: Typically three scape bracts below first flower and one floral bract subtending each flower; lanceolate; narrowly acute apex and truncate clasping base; entire margin; glabrous and matte abaxial and adaxial; scape bracts to about 30 mm long 10 mm across at base; floral bract to about 25 mm long and 8 mm across;

Scape bract color: Adaxial and abaxial edges nearest RHS 144C and centers nearest RHS between RHS N144A and RHS N144B;

Floral bract color: Adaxial and abaxial apical edges nearest RHS 147B, adaxial and abaxial inner portions nearest RHS NN155B with a faint blush of nearest RHS 76B;

Fruit and seeds: Have not been observed;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The new plant grows best and shows best coloration with plenty of moisture, adequate drainage and light shade, but is able to tolerate some drought when mature.

Hardiness: At least from USDA zone 3 through 8.

It is claimed:

1. A new and distinct *Hosta* plant named *Hosta* 'Gold Medal' as herein described and illustrated.

* * * * *